United States Patent [19]

Anderson et al.

[11] Patent Number: 4,767,935
[45] Date of Patent: Aug. 30, 1988

[54] SYSTEM AND METHOD FOR MEASUREMENT OF TRAVELING WEBS

[75] Inventors: Leonard M. Anderson, San Jose; Mathew G. Boissevain, Los Altos Hills; M. Kent Norton, Saratoga, all of Calif.

[73] Assignee: Measurex Corporation, Cupertino, Calif.

[21] Appl. No.: 902,225

[22] Filed: Aug. 29, 1986

[51] Int. Cl.$^4$ ............................................. G01N 21/85
[52] U.S. Cl. .................................... 250/571; 250/339; 356/429
[58] Field of Search ............... 250/571, 572, 559, 562, 250/563, 339, 341, 359.1, 360.1; 356/429, 430, 431, 434, 435; 162/198, 263, DIG. 6

[56] References Cited

U.S. PATENT DOCUMENTS

| | | |
|---|---|---|
| 3,655,980 | 4/1972 | Bossen ................................ 162/198 |
| 3,806,730 | 4/1974 | Tirkkonen et al. ............. 250/359.1 |
| 4,006,358 | 2/1977 | Howarth ............................. 162/198 |
| 4,124,300 | 11/1978 | Mead et al. ........................ 250/571 |
| 4,300,049 | 10/1981 | Sturm .................................. 250/339 |
| 4,577,104 | 3/1986 | Sturm .................................. 250/341 |

Primary Examiner—Edward P. Westin
Attorney, Agent, or Firm—Burns, Doane, Swecker & Mathis

[57] ABSTRACT

A system and method for optically measuring parameters such as dry basis weight of fibrous sheet materials during manufacture without scanning. The system includes mirror sections for reflecting modulated light as parallel rays perpendicularly incident upon one surface of a traveling web, and a plurality of light detection devices to detect light transmitted through the web at two distinct wavelengths. The system further includes ducts to environmentally isolate the mirror sections and the light detection devices.

22 Claims, 4 Drawing Sheets

SYSTEM AND METHOD FOR MEASUREMENT OF TRAVELING WEBS

BACKGROUND OF THE INVENTION

1. Field of the Invention

The present invention generally relates to a system and method for measuring properties of traveling webs of sheet material during manufacture and, more particularly, to a system and method for providing measurements such as dry basis weight of fibrous sheet materials.

2. State of the Art

In the art of making sheet materials, an important quality control measure is basis weight. "Basis weight" is normally defined as the weight per unit area of sheet material and is usually stated in units of grams per square inch. A related measure that is particulary useful during the manufacture of fibrous sheet materials, such as paper and cardboard, is known as "dry basis weight"; it refers to weight per unit area of sheet material excluding moisture. In the art of paper-making, dry basis weight is equivalent to the weight of dry material, primarily fibers, comprising a given area of a paper sheet.

It is well known that dry basis weight can be determined by laboratory tests but that such tests have several inherent drawbacks. One shortcoming, for example, is that substantial time is required for sample acquisition and analysis; during that time, substantial quantities of sheet material may be produced and production conditions may change. Another drawback of laboratory tests is that samples obtained for testing may not completely represent sheet material that is produced; this is because samples, for practical reasons, are often obtained only at the end of a sheet roll and, therefore, may not be representative of paper quality at intermediate locations.

It is also known that properties of sheet material can be detected by directing a beam of light or other radiation of known intensity against a surface of a sheet and measuring the radiation absorbed by the sheet. Generally speaking, the amount of absorbed radiation at a particular wave length is a function of the composition of the sheet material in accordance with Beer's law; for example, infrared light having a wavelength of about 1.5 microns is preferentially absorbed by cellulose fibers.

Various devices have been proposed for making on-line parametric measurements of properties of traveling webs of sheet material. (The term "-on line" refers to measurements that are made on a sheet-making machine while the machine is operating; the phrase "parametric measurements" refers to measurements of physical properties whose values determine characteristics and qualities of the sheet material.) Thus, parametric measurements of paper sheet and similar fibrous materials include basis weight, dry basis weight, moisture content, thickness, and transmissivity. In practice, accurate online parametric measurements during paper-making processes are especially difficult to make. The difficulties arise, in part, because modern papermaking machines are large and operate at high speeds; for example, conventional paper-making machines can produce sheets which are 100 to 400 inches wide at the rate of about 20 to 100 feet per second. Furthermore, on-line measurements are problematical in many paper-making factories because of severe environmental conditions; for example, the environment around a paper-making machine may inclue a high concentration of wet pulp and a humid atmosphere including water droplets and air-borne particles of sulfuric acid or alkalies To provide on-line parametric measurements of paper and other fibrous sheet materials, workers in the art have proposed various sensors that periodically traverse traveling webs of sheet material. (In the sheet-making art, the direction of sheet travel is known as the "machine direction" and the direction normal to machine direction is known as the "cross direction"; thus, a sensor that moves transversely of a traveling sheet can be said to scan in the cross direction.) For example, U.S. Pat Nos. 3,641,349; 3,681,595; 3,757,122; and 3,886,036 assigned to Measure Corporation discuss basis weight gauges of the scanning type. Also, U.S. Pat. No. 4,289,964, assigned to Intec Corporation, suggests that beta ray gauges can scan slowly across a traveling web in the cross direction to determine basis weight. Further, the Intec patent suggests that beta ray gauges can be augmented with laser, infrared, or ultraviolet light sensors to indicate transmissive qualities across the web; the augmenting sensors are desirable because beta ray sources usually require relatively long periods to generate statistically sufficient numbers of beta rays for measurement purposes.

Despite numerous advantages of scanning gauges in sheet-making operations, such gauges can have limitations. For example, when scanning gauges provide sample measurements infrequently, the measurements may not be optimal for reliable control purposes. This is because a relatively large number of measurements is required in many control situations to provide statistical confidence that a process change is required. In other words, responsive and accurate control often is not always possible with slow-moving scanning gauges. In view of such drawbacks of some scanning devices, it has been proposed to mount fixed sensors at locations distributed along the cross-direction of a traveling web of material. In particular, U.S. Pat. No. 3,806,730 suggests a measuring device that includes a set of radiation emitting tubes mounted to distribute light incident upon the surface of a moving web in the cross-direction. According to the patent, the light tubes are rectangular aluminum pipes that have bright interior surfaces and are filled with inert gas. A second set of similar tubes is positioned to receive light transmitted through the web and to carry that light to a detector. The device described in the patent is said to be useful for measuring parameters such as basis weight and moisture content of paper sheet materials.

As further background to the present invention, it is useful to describe a typical paper-making process. Generally speaking, a paper making process begins when a slurry of fibers and water, called "raw stock", is spread onto a supporting wire mesh from a reservoir called a "head box" through so-called "slice-lip openings." The wire mesh supports the fibers while allowing substantial drainage. To uniformly spread raw stock onto a wire mesh, it is customary to employ gate-like devices mounted next to one another in the cross direction at the slice lip openings. After a wet web is formed on a wire mesh, the web is passed through a press section to express water from the web. Then, the web is passed through a dryer section where water is evaporated from the web. After the dryer section, the web passes through calendar rollers and then usually through a scanner and onto a reel. The portion of a paper-making process prior to a dryer is often referred to as the "wet end" of the process, and the subsequent portion is called the "dry end". It can be appreciated that measurements at the wet end are highly desirable, because such measurements can permit control early in the paper production process and, thus, can minimize wastage by indicating needed process changes before substantial quantities of substandard paper are produced. On the other hand, wet end measurements are difficult to make because of the high water content (usually about 50%) of paper webs and frequently severe environmental conditions. Because of the environment, on-line measuring devices on sheet-making machines often share repair and maintenance problems with the host machines. However, since sheet-making machines often must operate continuously for extended periods, it is of practical importance that repair and maintenance of on-line measuring devices on such machines can be accomplished without causing down-time to the sheet-making machines.

OBJECTS AND SUMMARY OF THE PRESENT INVENTION

An object and advantage of the present invention is to provide an improved system and method for continuously determining properties, such as dry basis weight, across profiles of traveling webs of sheet material without scanning the webs.

In accordance with the preceding object, the present invention provides a system including: illuminating means to transmit substantially parallel rays of light generally perpendicularly onto one surface of a traveling web simultaneously and uniformly across substantially the entire width of the web; a plurality of light detection devices to receive parallel rays of light transmitted through the web at least at two distinct narrow bands of wavelengths; enclosure means to provide environmental isolation of the illuminating means and the detection devices; and signal processing means to indicate the quantity of light received by the detection devices at identifiable locations across a profile of the web.

In a particular embodiment, the present invention provides a system including first and second ducts each having a transparent wall mounted to extend transversely across opposite faces of the traveling web of sheet material. In one of the ducts, a light source transmits collimated beams of light along the length of the duct and reflectors reflect the beams as parallel rays generally perpendicularly incident upon the surface of the web. In the other duct, light detection devices receive parallel rays transmitted through the web at least at two distinct narrow bands of wavelengths. Signal processors are connected to the detection devices for indicating the quantity of light transmitted through the web at identifiable locations.

Further, the present invention provides a method for optically determining properties of a traveling web of sheet material without scanning. The method includes the steps of providing modulated beams of collimated light; reflecting parallel rays from the collimated beams generally perpendicularly onto the surface of a traveling web across substantially the entire width of the web; detecting parallel ray transmitted through the traveling web; and providing electrical output signals proportional to the intensity of detected light at two distinct or narrow bands of wavelengths at identifiable locations along a profile of the web.

The foregoing and other aspects of the present invention can be readily ascertained by reference to the following description and attached drawings which illustrate the preferred embodiment.

DETAILED DESCRIPTION OF THE PREFERRED EMBODIMENT

Figure 1:
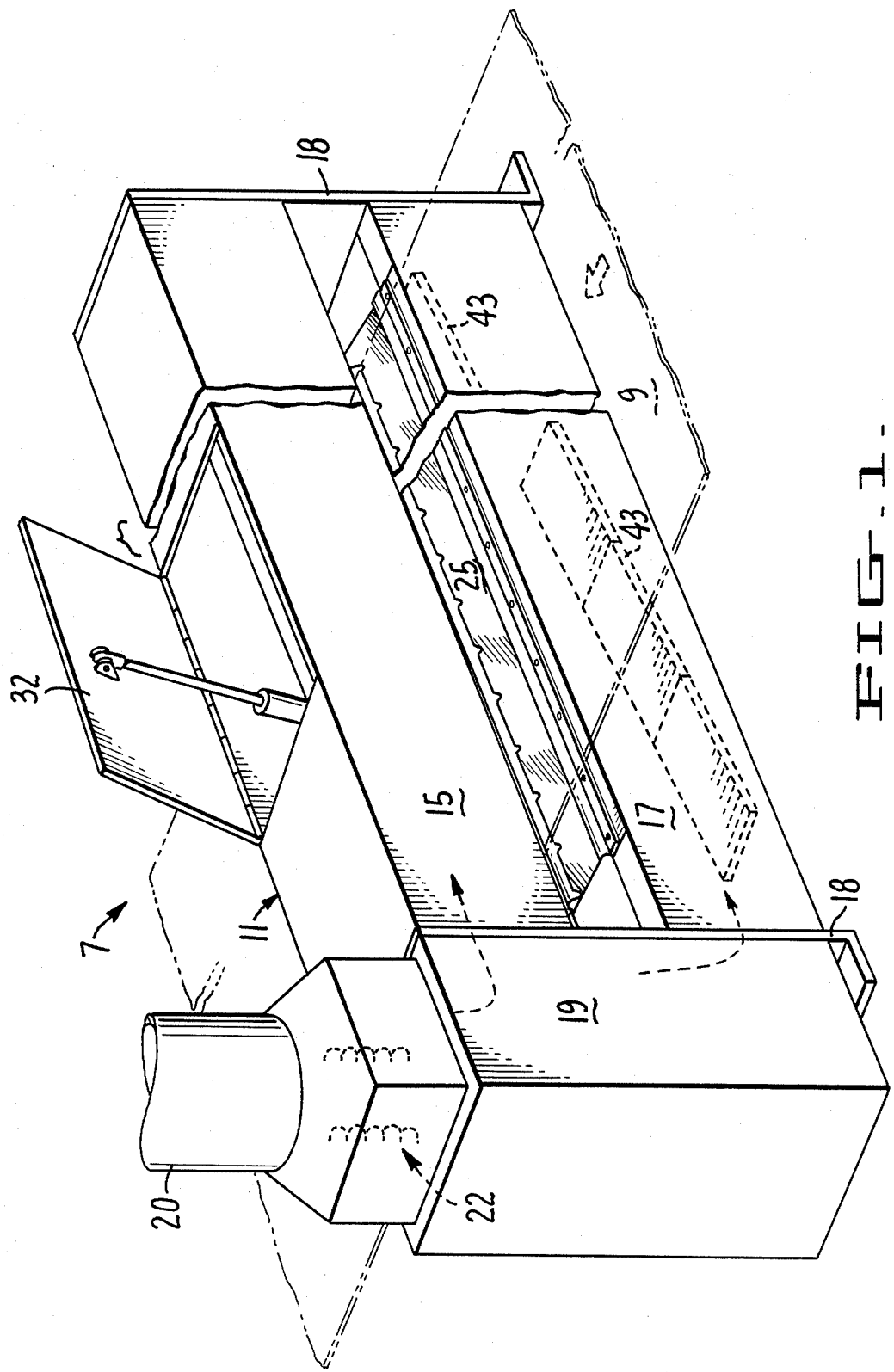
FIG. 1 is a pictorial view of the exterior of a housing of a machine according to the present invention with internal components generally indicated by dashed lines.

FIG. 1 shows a machine 7 for providing parametric measurements of a web 9 of sheet material traveling horizontally in the direction indicated by the arrow. Machine 7 generally includes a housing 11 that protectively isolates measurement instruments and components in ducts 15 and 17 which are supported at their opposite ends by upstanding stanchions 18. In typical installations, ducts 15 and 17 range in length from about 100 inches to about 400 inches and are spaced apart vertically by a distance of about eight inches to allow clearance for web 9 to travel between the ducts.

Further in the preferred embodiment of machine 7, ducts 15 and 17 are connected in gas flow communication with a cross duct 19, and pressurized air is provided to the ducts via inlet duct 20. Thermostatic controls 21 and heaters 22 (FIG. 2) are provided in housing 11 to maintain the pressurized air sufficiently above dew point temperature to prevent condensation from forming on the surfaces of the ducts 15 and 17. In practice, the temperature within the ducts is usually about 100° F., thermostatic control 21 includes a conventional thermistor 21A, and heater 22 is a conventional electric heater proportionally controlled by thermistor 21A.

Figure 2:
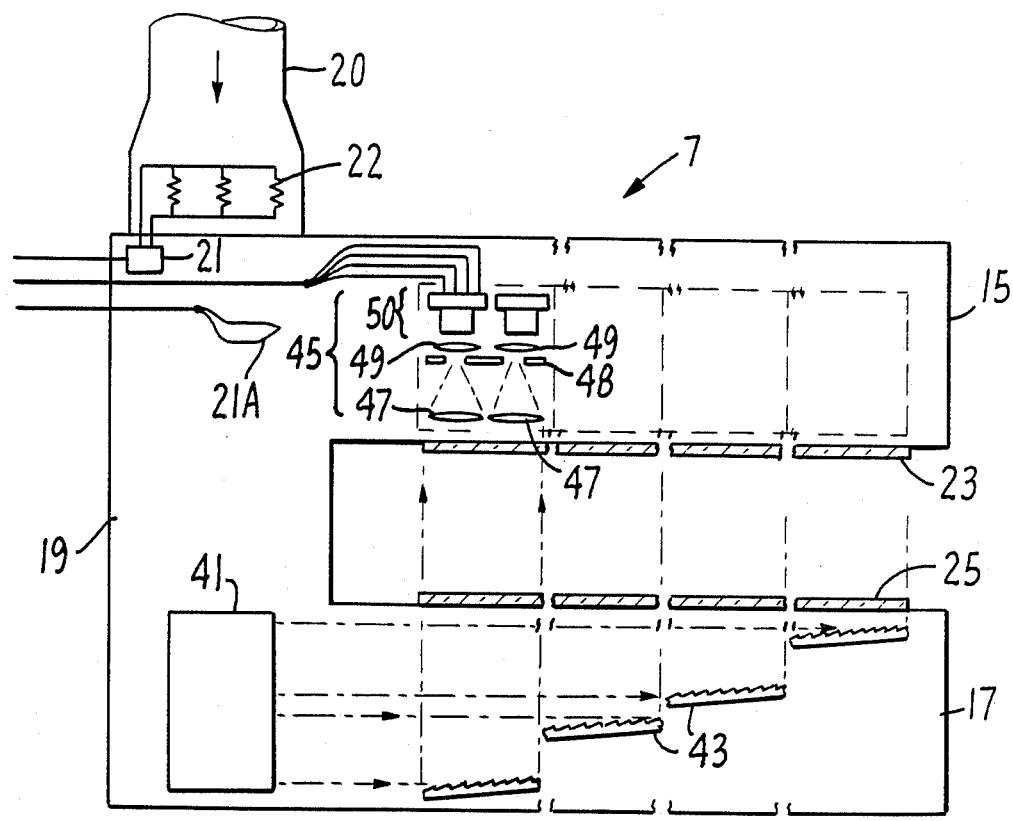
FIG. 2 is a schematic diagram of a machine according to the present invention; this diagram is generally oriented as a vertical cross-section taken lengthwise through the machine of FIG. 1.

As best shown in FIG. 2, ducts 15 and 17 have transparent walls 23 and 25, respectively, that provide line-of-sight optical communication between the interiors of the ducts as indicated schematically by the vertical arrows. (That is, the interior of one of the ducts can be viewed from the interior of the other duct in the absence of web 9.) In the embodiment shown in the drawings, transparent walls 23 and 25 each comprise a single glass pane extending across the length of the duct, but a series of separate windows formed of glass or other transparent materials can be utilized. In practice, transparent walls 23 and 25 are about three inches wide.

Figure 3:
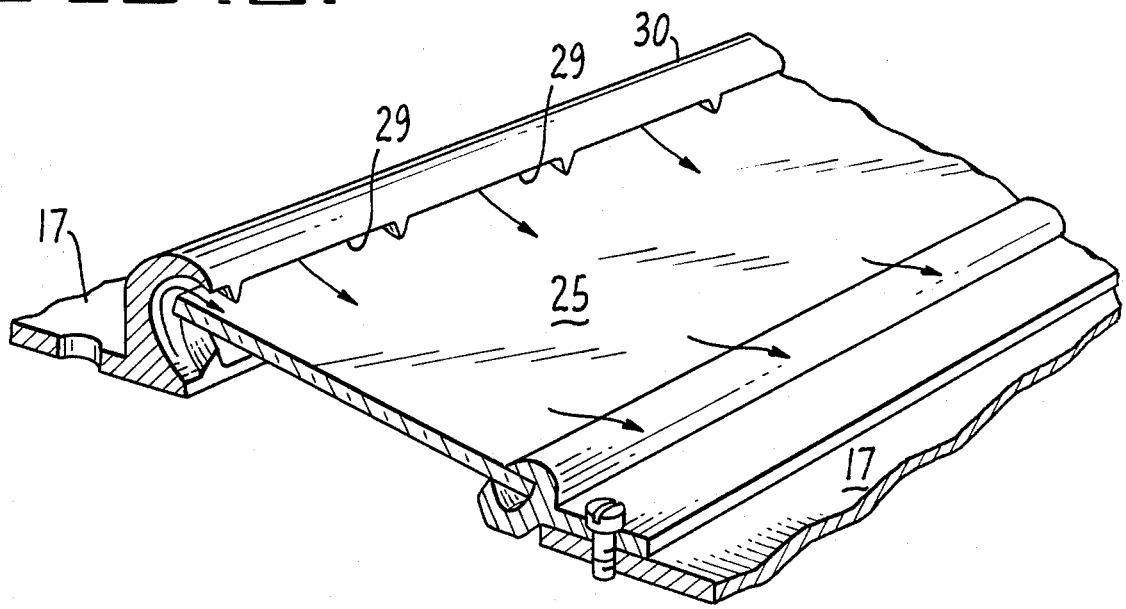
FIG. 3 is a pictorial view, drawn to an expanded scale for purposes of illustration, of a portion of the machine of FIG. 1.

For practical use of machine 7 in a factory environment, transparent walls 23 and 25 must be kept substantially free from accumulations of dust and other particles that may interfere with transmission of light through the walls. A suitable cleaning means to prevent such accumulations is illustrated in FIG. 3 in conjunction with transparent wall 25; a similar cleaning means can be provided to keep transparent wall 23 free from accumulations of particles. Generally speaking, the illustrated cleaning means produces air flows, indicated by the curved arrows, that sweeps the exterior surfaces of wall 25. More particularly, the air flows are discharged from spaced-apart channels 29 formed in an elongated frame member 30 that supports one side of wall 25. The exterior open ends of channels 29 are oriented to direct air flow across the exterior surface of wall 25 as indicated. The interior open ends of channels 29 are in communication with the interior of duct 17 so that air flow through channels 29 is driven by pressurized air carried by the duct. Preferably, channels 29 are spaced along the full length of transparent walls 23 and 25. In practice, transparent walls 23 and 25 are slightly canted from horizontal to promote water drainage from their surfaces.

Figure 5:
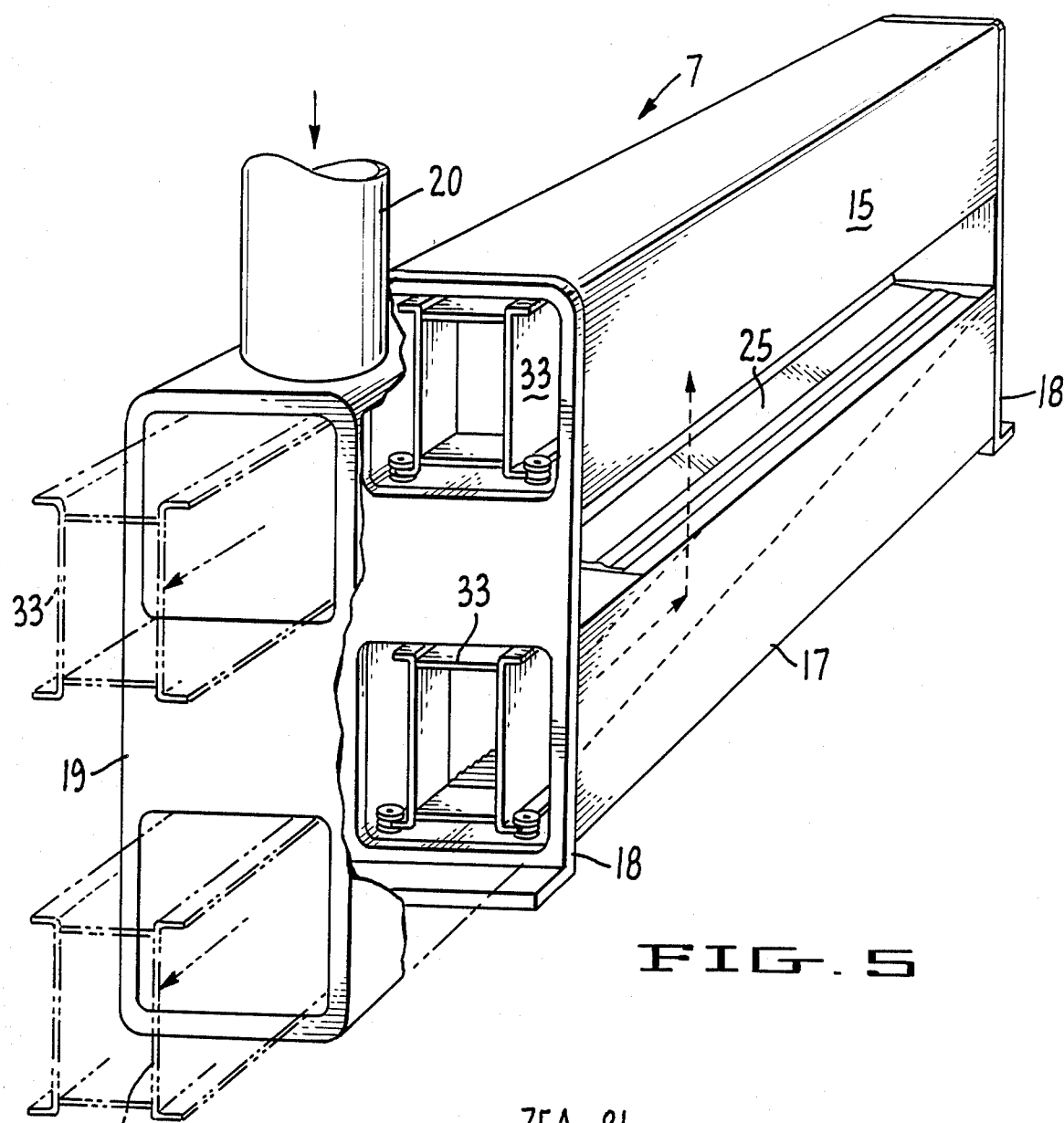
FIG. 5 is a pictorial view, partially cutaway, showing certain internal components of the machine of FIG. 1, with components in displaced positions shown by dashed lines.

Further for practical use and maintenance of machine 7, convenient access must be provided to components within the machine. Thus, in the embodiment of FIG. 1, doors 32 are mounted along the length of ducts 15 to provide access to the interior of the duct. The embodiment in FIG. 5 particularly shows sliding tray-like mechanisms 33 that are mounted to extend lengthwise within upper and lower ducts 15 and 17. The tray-like mechanisms 33 each have a box-like configuration and include runners, or wheels, to travel within ducts 15 and 17. In use, tray-like mechanisms 33 carry measurement instruments and components utilized in machine 7. To gain access to the instruments and components, the ends of duct 15 and 17 are opened and tray-like mechanisms 33 are slidably removed as indicated by dashed lines in FIG. 5.

Referring again to FIG. 2, operative measurement components of machine 7 include a light source 41 mounted at one end of duct 17, a mirror array 43 mounted along the length of duct 17 to reflect source light through transparent wall 25 along substantially the entire cross-directional extent of web 9, and sets of light detection devices generally indicated by bracket 45 mounted in duct 15 to receive light transmitted through transparent wall 23. More particularly, light source 41 is positioned to direct beams of collimated light generally parallel to the longitudinal centerline of the duct. Mirror array 43 is stationarily mounted to receive and decompose the collimated beams to provide parallel rays directed through transparent wall 25 generally perpendicular to the surface of web 9 along substantially its entire width.

Figure 4:
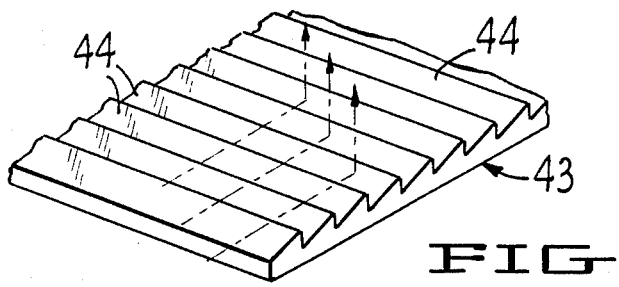
FIG. 4 is a pictorial view of a detail of an array of mirrors for use in the machine of FIG. 1.

Referring now to FIG. 4, mirror array 43 comprises staggered slanting mirror sections 44 mounted on a generally planar base. In profile, slanting mirror sections 44 provide a continuous saw-tooth-like configuration. In practice, slanting mirror sections 44 each have an angle of about 43° from horizontal and the base of mirror array 43 is mounted in duct 17 at a slight angle from horizontal, usually about 2°, so that the mirror array 43 extends as a ramp along the length of duct 17 in the path of light beams from source 41. Thus, as shown in FIGS. 1 and 2, the staggered slanting sections 44 decompose beams of collimated light from source 41 into parallel rays directed substantially vertically and extending along the length of transparent wall 25. In practice, the practical length of mirror array 47 is less than about eighteen feet; accordingly, if web 9 is wider than about eighteen feet, two mirror arrays are utilized and a light source is located at each end of duct 17. (A complete machine in such an embodiment would also usually have a cross duct 19 at each end.)

Figure 6:
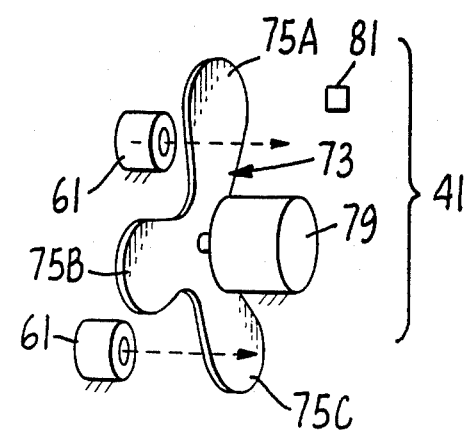
FIG. 6 is an exploded pictorial view of details of a light source assembly for use in the machine of FIG. 1.

In FIG. 6, an assembly comprising a preferred embodiment of light source 41 is shown. In this embodiment, light source 41 includes two illuminating devices 61 fixedly mounted at the end of duct 17. (If illuminating devices 61 are mounted to direct light perpendicular to the side of housing 11, deflecting mirrors can be provided to deflect collimated beams generally parallel to the centerline of duct 17.) In practice, illuminating devices 61 are conventional incandescent lamps and each includes a parabolic reflector member to form a collimated beam of generally parallel rays. Preferably, illuminating devices 61 emit a broad band of visible and infrared light including light within the wavelength band between 1.3 and 2.1 microns. The number of illuminating devices 61 is a matter of design choice.

Referring still to FIG. 6, light source 41 further includes a modulating mechanism. In the embodiment shown in FIG. 6, the modulating mechanism includes a rotatably mounted rotor member 73 having three symmetrical vanes 75A, 75B, and 75C that radially extend at about 120° intervals from the center of rotation. Rotor member 73 is rotatably mounted such that vanes 75A, 75B and 75C simultaneously block or unblock light from illuminating devices 61 depending upon the angular position of the vanes. In usage, rotor member 73 is rotatably driven by a motor 79 so that the beams produced by illuminating devices 61 and 63 are simultaneously modulated. As also shown in FIG. 6, a stationarily-mounted position detector 81 is provided to detect the rotational position of vanes 75A, 75B and 75C. Position detector 81 can be a paired light-emitting diode and phototransistor as is shown in FIG. 8.

Figure 7:
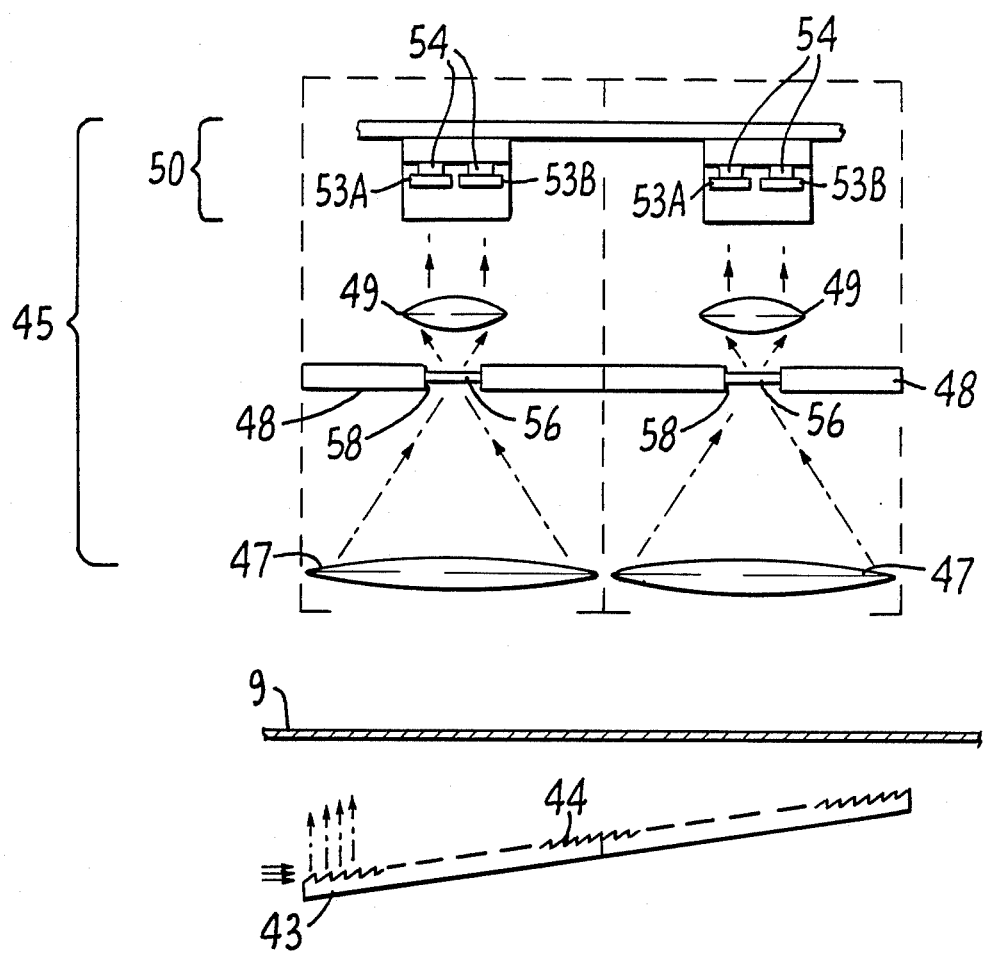
FIG. 7 is a detailed view, drawn to an enlarged scale for purposes of explanation, of a light detection assembly for use in the machine of FIG. 1.

Referring now to FIG. 7, each set 45 of light detection devices includes components for collimating, filtering and sensing substantially parallel light rays that have been transmitted through web 9 perpendicular to the web surface. In the preferred embodiment, each set 45 of detection devices includes a converging lens 47 followed by a narrow aperture plate 48 stationarily placed at the focal point of lens 47. Also in each set 45, a second converging lens 49 is spaced from aperture plate 48 by a distance approximately equal to the focal length of lens 49. In practice, lenses 47 and 49 can be Fresnel-type lenses. Following lens 49 is a pair of side-by-side light detectors generally indicated by bracket 50. Each member of the pair of detectors 50 includes a photoelectric transducer 54 such as is conventionally made from lead sulfide. A first narrow bandpass optical filter 53A is mounted adjacent the first of the photoelectric transducers 54 of the pair, and a second narrow bandpass optical filter 53B is mounted adjacent the second of the transducers of the pair. Bandpass filters 53A and 53B differ from each other in terms of the bands of wavelengths of light that they pass. In papermaking operations, for example, bandpass filter 53A could be selected to pass light in a narrow band of wavelengths about a mean value of 1.5 microns, or in a narrow band of wavelengths about a mean value of 2.1 microns; and, bandpass filter 53B could be selected to pass light in a narrow band of wavelengths about a mean value of 1.3 microns or in a narrow band of wavelengths about a mean value of 1.8 microns. The wavelengths of light passed by filter 53A can be called the "measurement" wavelengths and the wavelengths passed by filter 53B can be called the "reference" wavelengths. In practice, pairs of bandpass filters 53A and 53B and associated photo electric transducers 54 are mounted side by side in the cross direction as shown in FIGS. 2 and 7, or are aligned with each other in the machine direction. Also in practice, sets 45 of light detection devices are mounted side-by-side in duct 15 in series, as partially shown in FIG. 7, with the sets 45 spaced apart from each other about every three to six inches across the entire width of web 9; in other words, it is usually desirable to take a measurement at the reference wavelengths and at the measurement wavelengths about every six inches in the cross direction to obtain a complete profile of web 9.

As further shown in FIG. 7, it is often desirable to mount thin diffusing sheets 56 of film across apertures 58 in aperture plate 48. The purpose of diffusing sheets 56 is to provide mixing of light rays passed through apertures 58. In practice, diffusing sheets 56 are formed of Teflon, but other materials are suitable; also, diffusing lenses can be used in place of sheets 56 at apertures 58 to mix light rays passing through the apertures.

Figure 8:
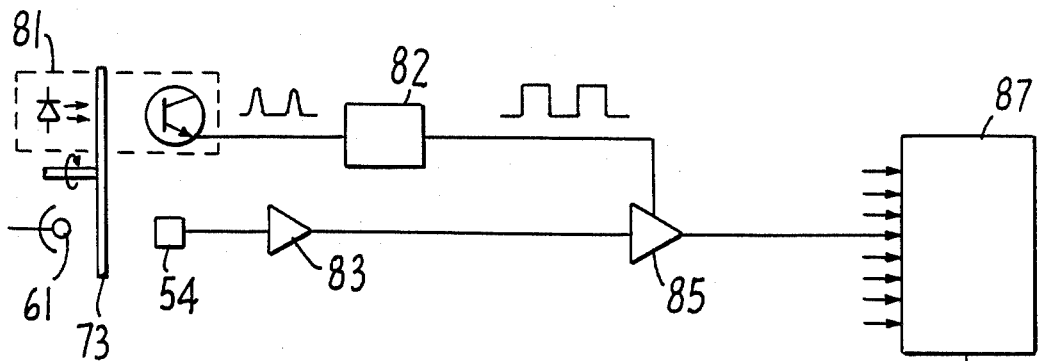
FIG. 8 is a functional diagram of an electronic system for processing signals obtained by the machine of FIG. 1.

Referring now to FIG. 8, an electronic system is shown for processing electrical signals produced by the pairs of photoelectric transducers 54, thereby to provide output signals indicative of optical properties of examined profiles of web 9. The electronic system includes position detector 81 connected to provide output signals to a pulse converter 82 that converts the signals concerning the rotational location of rotor 73 into square-wave signals. The electronic system of FIG. 8 further includes a preamplifier 83 connected to each of the photoelectric transducers 54 to amplify their analog output signals. A demodulator 85 is connected to preamplifier 83 to demodulate the amplified transducer signals using the square-wave position signals from converter 82 for timing coordination. Output signals from demodulator 85 are normally direct current (DC) signals having amplitudes proportional to the intensity of light received by photoelectric transducers 54. Because of narrow bandpass filters 53A and 53B, and because modulation by rotor member 73 is coordinated with pulse converter 82, the analog signals from transducer 54 are substantially undisturbed by extraneous sources of light. As further shown in FIG. 8, demodulated signals derived from each of the transducers 54 are placed in serial order by a multiplexer 87. The multiplexed analog signals are then converted to digital signals by a conventional analog-to-digital converter 89 for transmission to a computer. The components in the system of FIG. 8 (i.e., pulse converter 82, preamplifier 83, demodulator 85, multiplexer 87, and analog-to-digital converter 89) are of conventional design and are well known in the signal processing art.

Complete operation of machine 7 will now be described. To begin operation, pressurized air is introduced via inlet duct 20 and is circulated through ducts 15 and 17 via cross duct 19. The circulating air is maintained above ambient temperature by thermostatic control 21 and heater 22, and serves to cool light detection devices 45. Also the circulating air heats the walls of duct 15 to prevent condensation of water vapor on its surfaces; this has the practical advantage of preventing condensation from dropping onto web 9 or otherwise interfering with operation of machine 7. Further, the circulating air in ducts 15 and 17 provides positive pressure to create air flows to sweep the surfaces of transparent walls 23 and 25, as shown in FIG. 3. Still further, the circulating air keeps mirror array 43 free of dust by providing pressurization sufficient to prevent dust particles from entering duct 17. In view of the foregoing description, it can be appreciated that the apparatus and system of the present invention is suitable for usage in severe environments such as near the first press section of a paper-making machine.

To measure optical properties of a traveling web 9, illuminating devices 61 are activated and rotor 73 is rotatably driven to modulate the emitted light. When illuminating devices 61 are not simultaneously blocked by vanes 75A-75C of rotor 73, collimated light beams from the illuminating devices extend along duct 17 and are reflected by the staggered slanting section 44 of mirror array 43. The reflected beams form parallel rays directed upward through transparent wall 25 generally perpendicular to the surface of adjacent web 9 along the length of mirror array 43. The practical effect of providing parallel rays that are directed perpendicularly incident upon web 9 is that measurements of transmissive properties of the web are substantially independent of the vertical location of the web surface between ducts 15 and 17 and, thus, are independent of fluttering of the web. By way of contrast, if emitted rays were not parallel or were not perpendicularly incident upon the surface of web 9, the quantity of light detected by photoelectric detectors 54 could vary depending upon the elevation of the surface of web 9. Such variations, if present, would complicate accurate determination of properties of web 9.

Rays that emerge generally perpendicularly from the surface of web 9 and pass through transparent wall 23 are focused by converging lenses 47 toward apertures 56 in plates 48. The ones of the focused rays that pass through the apertures 58 in plates 48 diverge until they reach converging lenses 49 and are re-focused. The focused parallel rays then pass through bandpass filters 53A and 53B and strike photoelectric transducers 54. Diffusing sheets 56 at apertures 58 assure that rays reaching both transducers 54 in the sets 50 are representative of the same inspected area of web 9. Because of optical bandpass filters 53A and 53B, light is detected at two distinct narrow bands of wavelengths in the infrared spectrum. In practice, the detected wavelengths are selected such that the measurement wavelength is preferentially absorbed by the sheet material of web 9 and the reference wavelength is less substantially absorbed. In the case where web 9 comprises paper sheet material, for example, the measurement wavelength is normally chosen for specific absorptions by cellulose fibers and the reference wavelength is chosen to be near, but outside, the resonant absorption band of cellulose. For instance, the measurement wavelength for cellulose can be approximately 1.5 microns, and the reference wavelength can be approximately 1.3 microns.

The converging lenses 47, aperture plates 48 and converging lenses 49 generally operate to collect only rays that emerge substantially perpendicular to the web surface. Because the collected rays are generally parallel to one another, this further assures that measurements of transmissive properties of web 9 are substantially independent of the elevation of the web relative to photoelectric transducers 54 and, therefore, that measurements are relatively unaffected by fluttering of web 9. As a result, this measurement technique minimizes false indications of required changes in process conditions and increases the accuracy of the detection system.

Electrical output signals from photoelectric transducers 54 can be processed by the system of FIG. 8 to provide a series of digital output signals for each associated pair of photoelectric transducers 54. Output digital signals representing the intensity of light received at the measurement wavelengths and digital signals representing the intensity of light received at the reference wavelengths can be combined to provide a measure of the properties of the inspected area of web 9. One particularly useful measurement of such properties is dry basis weight; for many papermaking operations, dry basis weight can be expressed in terms of the two detected wavelengths as follows:

$$DBW = A - B \ln \frac{REF \text{ on sheet}}{REF \text{ no sheet}} + C \ln \frac{MEAS \text{ on sheet}}{MEAS \text{ no sheet}}$$

wherein:

DBW is dry basis weight of the inspected area of sheet material;

A, B and C are constants;

"ln" indicates the natural logarithmic function;

"REF on sheet" is the output of a reference detector when sheet material is present in the gap between ducts 15 and 17;

"REF no sheet" is the output of a reference detector in the absence of sheet material in the gap between ducts 15 and 17;

"MEAS on sheet" is the output of a measurement detector when sheet material is present in the gap between ducts 15 and 17; and "MEAS no sheet" is the output of a measurement detector when sheet material is absent from the gap between ducts 15 and 17.

It should be appreciated that measurements according to the preceding equation can be made for each pair of transducers 54 and associated pair of bandpass filters 53A and 53B across web 9. The total set of such measurements for a given cross-sectional profile of web 9 yields a sequence of outputs from analog-to-digital converter 89. For any given profile, the origin location of each measurement can be readily determined; for example, a measurement made at 4.5 feet from left margin of web 9 can be easily identified. Identification of the origin location of measurements permits precise control of production conditions at identified cross-direction locations by, for example, automatically controlling slice lip openings at headboxes for the paper-making machine. In practice, profile measurements are produced sufficiently rapidly to provide process control during start-ups, grade changes, and upsets. Also, controls based upon rapid profile measurements can reduce sheet variations in the machine direction during steady-state operation and can reduce process sensitivity to periodic instabilities.

It should also be appreciated that the use of two narrow bands of wavelengths permit substantial accuracy of measurement and minimize dependence on variations in sheet properties such as moisture content, material composition and temperature; and on environmental conditions such as dirt or moisture on transparent walls 23 and 25, steam, source lamp intensity and height of web 9. In any application of machine 7, the above-mentioned constants A, B and C may be optimized to give the best measurement accuracy for those variations which are present.

Although the present invention has been described with particular reference to the preferred embodiment, such disclosure should not be interpreted as limiting. Other alterations and modifications will no doubt become apparent to those skilled in the art after having read the preceding disclosure. For example, circulation of pressurized air through ducts 15 and 17 can be individually provided and, thus, cross duct 19 might be eliminated. Also, machine 7 may include light collimating devices, such as socalled honeycomb filters, to provide additional collimation of light passing through transparent walls 23 and 25; such filters can further minimize variations due to flutter or elevation change of web 9 within the vertical gap between ducts 15 and 17. Also, although the preceding description has described a single array of mirrors 43, a multiplicity of mirror arrays can be used. Still further, additional measurements of basis weight and sheet moisture can be made at the reel end of a paper machine and can be used for calibration purposes and to correct for long-term signal drift. In view of such variations and others, it is intended that the appended claims be interpreted as covering all alternative embodiments and equivalents as fall within the spirit and scope of the present invention.

We claim:

1. A system for providing measurments, such as dry basis weight, of traveling webs of sheet material comprising:
   (a) illuminating means for directing substantially parallel rays of light substantially perpendicularly onto one surface of a traveling web simultaneously across substantially the entire width of the web;
   (b) a plurality of light detecting means to detect substantially parallel rays of said light emerging from the web perpendicular to the web surface;
   (c) enclosure means that environmentally isolate the illuminating means and the detecting means; and
   (d) signal processing means connected to the light detecting means for generating signals indicative of the quantity of light detected.

2. A system as defined in claim 1 wherein the enclosure means includes first and second ducts that extend across opposite faces of the traveling web to house, respectively, the illuminating means and the light detecting means.

3. A system as defined in claim 2 wherein said first and second ducts each have at least one transparent wall to provide line-of-sigt communication between the interiors of the ducts across the width of the travelling web.

4. A system as defined in claim 3 further including means to admit pressurized air into the first and second ducts, and means to direct pressurized air to sweep particles from the exterior surfaces of said transparent walls.

5. A machine for providing optical measurements of properties of a traveling web of sheet material comprising:
   (a) a first duct mounted to extend across one face of a web;
   (b) a second duct mounted to extend substantially parallel to the first duct across the opposite face of the web;
   (c) a first transparent member forming a wall of the first duct and a second transparent member forming a wall of the second duct, said first and second transparent members being located generally opposite one another to provide line-of-sight communication between the interiors of the said first and second ducts substantially across the width of the traveling web;

(d) means to make optical measurements of properties of the web traveling between the first and second ducts by transmitting generally parallel rays of light perpendicularly onto the web via the first transparent member and detecting the intensity of substantially parallel rays of light emerging from the web substantially perpendicular to the web surface via the second transparent member.

6. A machine according to claim 5 wherein the first and second ducts are connected in gas flow communication to receive pressurized air.

7. A according to claim 6 further including heater means to heat air within the ducts and thermostatic control means to control the heater means.

8. A machine according to claim 5 further including mechanisms that slidably extend lengthwise within the first and second ducts for carrying the means to make optical measurements of the traveling web.

9. A machine according to claim 6 further including means to direct pressurized air from the interiors of the ducts to sweep across the first and second transparent members to prevent accumulations of particles thereon.

10. A system for determining optically-sensitive properties of traveling webs of sheet material during manufacture without scanning comprising:
(a) first duct means mounted to extend transversely of one face of a traveling web, the duct means having a transparent wall facing the web;
(b) light source means arranged to direct collimated light lengthwise along the interior of the first duct means;
(c) reflector means mounted within the first duct means to reflect said beams as parallel rays directed through said transparent wall generally perpendicular to the surface of the web to illuminate substantially the full width of the web;
(d) second duct means mounted to extend generally parallel to the first duct means adjacent the opposite face of the sheet and having a transparent wall facing the sheet;
(e) a plurality of light detector means mounted within the second duct to detect substantially parallel rays emerging frim the web, generally perpendicular to the web surface, said plurality of detector means being operable to provide electrical signals related to the optical intensity of the received light from identifiable locations across the web surface.

11. A system according to claim 10 wherein the reflector means comprises an array of reflecting surfaces having, in profile, a generally continuous saw-tooth configuration.

12. A system according to claim 11 wherein said array is mounted with said saw-tooth surfaces at progressively higher elevations.

13. A system according to claim 12 further including a rotor having spaced-apart vanes to modulate light emitted from said light source means.

14. A system according to claim 13 wherein said rotor has equally-spaced vanes.

15. A system according to claim 10 wherein the detector means comprises pairs of photoelectric transducers and associated optical filters with one said filter of each said pair being selected to pass a wavelength of light preferentially absorbed by at least one material comprising the web and the other said filter of each said pair being selected to pass a wavelength of light outside of the resonant absorption band of said at least one material.

16. A system according to claim 15 further including collecting means to collect parallel rays of light transmitted through the web generally perpendicular to its surface for detection.

17. A system according to claim 16 wherein the collecting means includes sets of two convering lenses with an aperture plate mounted therebetween and spaced from the lenses by distances generally equal to their focal lengths.

18. A system according to claim 16 including modulating means to modulate emitted light and coordinating means for timing operation of said modulating means and the light detector means.

19. A method for optically determining properties of traveling webs of sheet material without scanning comprising the steps of:
(a) transmitting modulated beams of collimated light through a duct;
(b) reflecting rays from the modulated beams through a transparent wall such that the rays are parallel and are generally perpendicularly incident upon the surface of a traveling web to simultaneously and uniformly illuminate substantially the full width of the web;
(c) detecting the intensity of generally parallel rays transmitted through the web generally perpendicular to the web surface at a plurality of adjacent locations; and
(d) and providing electrical output signals proportional to the detected light intensity at least at first and second narrow bands of wavelengths at identifiable ones of said plurality of locations.

20. A process according to claim 19 wherein light at the first detected wavelength is preferentially absorbed by at least one material comprising the web and light at the second detected wavelength is substantially outside of the resonant absorption band of said one material.

21. A process according to claim 20 further including the step of collecting rays of light transmitted through the web and then diffusing the collected rays.

22. A process according to claim 20 including the step of computing the dry basis weight at selected inspected locations on the web according to the following equation:

$$DBW = A - B \ln \frac{REF \text{ on sheet}}{REF \text{ no sheet}} + C \ln \frac{MEAS \text{ on sheet}}{MEAS \text{ no sheet}}$$

wherein:
DBW is dry basis weight of the inspected section of the web of sheet material;
A, B and C are constants;
"ln" is the natural logarithmic function;
"REF on sheet" is the detected intensity at the first wavelength band when sheet material is present;
"REF no sheet" is detected intensity at the first wavelength band in the absence of sheet material;
"MEAS on sheet" is detected intensity at the second wavelength band when sheet material is present; and
"MEAS no sheet" is detected intensity at the second wavelength band in the absence of sheet material.

* * * * *